US012740770B2

(12) United States Patent
Nguyen et al.

(10) Patent No.: US 12,740,770 B2
(45) Date of Patent: Sep. 22, 2026

(54) NASAL SPECIMEN COLLECTION SYSTEM

(71) Applicant: Board of Regents of the University of Nebraska, Lincoln, NE (US)

(72) Inventors: Thang Nguyen, Omaha, NE (US); Michael Wadman, Omaha, NE (US); Wesley Zeger, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 363 days.

(21) Appl. No.: 18/550,838

(22) PCT Filed: Mar. 23, 2022

(86) PCT No.: PCT/US2022/021481
§ 371 (c)(1),
(2) Date: Sep. 15, 2023

(87) PCT Pub. No.: WO2022/204241
PCT Pub. Date: Sep. 29, 2022

(65) Prior Publication Data
US 2024/0156442 A1 May 16, 2024

Related U.S. Application Data

(60) Provisional application No. 63/166,322, filed on Mar. 26, 2021.

(51) Int. Cl.
*A61B 10/00* (2006.01)
*A61M 3/02* (2006.01)

(52) U.S. Cl.
CPC ....... *A61B 10/0051* (2013.01); *A61M 3/0262* (2013.01); *A61M 3/0283* (2013.01); *A61M 2210/0618* (2013.01)

(58) Field of Classification Search
CPC ........ A61B 10/0051; A61B 2010/0216; A61B 10/0045; A61B 10/02; A61M 3/0262;
(Continued)

(56) References Cited

U.S. PATENT DOCUMENTS 3,005,564 A 10/1961 Weichselbaum
D281,534 S 11/1985 Ushikubo
(Continued)

FOREIGN PATENT DOCUMENTS

CA 45072 S 3/1979
CN 110101416 A 8/2019
(Continued)

OTHER PUBLICATIONS

Amazon et al., "Haakaa: Silicone Baby Nasal Aspirator", Haakaa, Amazon.com, Inc., 2022, 11 pp., Retrieved from the Internet on Dec. 9, 2024 from https://www.amazon.com/haakaa-Silicone-Aspirator-Easy-Squeeze-Transparent/dp/B09Q61B4MM/.
(Continued)

*Primary Examiner* — Adam J Eiseman
*Assistant Examiner* — Lucy Eppert
(74) *Attorney, Agent, or Firm* — Shumaker & Sieffert, P.A.

(57) ABSTRACT

An apparatus for collecting a nasal specimen includes a device body with a nozzle at a distal end of the device body. The nozzle is configured to interface with a nasal cavity. The apparatus further includes an irrigation path and a collection path within the device body. The collection path may be separate from the irrigation path. The irrigation path is configured to direct a fluid from an irrigation chamber into the nasal cavity in order to dislodge a sample from the nasal cavity. When the fluid flows back out of the nasal cavity, the
(Continued)

collection path is configured to direct at least a portion of the fluid and the sample dislodged from the nasal cavity into a collection chamber.

13 Claims, 23 Drawing Sheets

(58) Field of Classification Search
CPC ........ A61M 3/0283; A61M 2210/0618; A61M 2209/06; A61M 3/0279; A61M 3/0287; A61H 2201/0157; A61H 2201/105; A61H 2201/1253; A61H 2205/023; A61H 35/04
See application file for complete search history.

(56) References Cited

U.S. PATENT DOCUMENTS

| | | | |
|---|---|---|---|
| 4,859,423 | A | 8/1989 | Perlman |
| D307,052 | S | 4/1990 | Baxter |
| 6,135,358 | A | 10/2000 | Ballini |
| D559,397 | S | 1/2008 | Eriksson et al. |
| D613,873 | S | 4/2010 | Jia |
| D863,550 | S | 10/2019 | Melendez et al. |
| D888,274 | S | 6/2020 | Khalaj |
| D925,760 | S | 7/2021 | Tan et al. |
| D971,432 | S | 11/2022 | Best |
| D978,376 | S | 2/2023 | Ou |
| D979,788 | S | 2/2023 | Park |
| D990,694 | S | 6/2023 | Wu |
| 2011/0308336 | A1 | 12/2011 | Harmston et al. |
| 2014/0121592 | A1 | 5/2014 | Rubin et al. |
| 2018/0093034 | A1 | 4/2018 | Tsang et al. |
| 2019/0209746 | A1 | 7/2019 | Baker et al. |
| 2020/0353154 | A1 | 11/2020 | Schultz |

FOREIGN PATENT DOCUMENTS

| | | | |
|---|---|---|---|
| CN | 306453218 | S | 4/2021 |
| CN | 307792574 | S | 1/2023 |
| EP | 2424590 | A1 | 3/2012 |
| FR | 3001636 | A1 | 8/2014 |
| WO | 2010126586 | A1 | 11/2010 |
| WO | 2022029480 | A1 | 2/2022 |

OTHER PUBLICATIONS

Amazon et al., "Ozxno: Plastic Tube Cryovial Cryogenic Vial", OZXNO, Amazon.com, Inc., 2022, 5 pp., Retrieved from the Internet on Dec. 9, 2024 from https://www.amazon.com/OZXNO-Graduated-Plastic-Cryovial-Cryogenic/dp/B09TJ9BBM8.

Amazon et al., "Vakly: Plastic Graduated Triangular Intake Output Container", Vakly, Amazon.com, Inc., 2016, 7 pp., Retrieved from the Internet on Dec. 9, 2024 from https://www.amazon.com/Nakly-Graduated-Triangular-Laboratory-Container/dp/B01M0QP8LI/.

Amazon, "Acu-life: Nasal Aspirator", Apothecary Products, LLC, Amazon.com, Inc., 2009, 7 pp., Retrieved from the Internet on Dec. 9, 2024 from URL: https://www.amazon.com/Acu-Life-400004-Nasal-Aspirator/dp/B001T8S82Y/.

Extended Search Report from counterpart European Application No. 22776541.9 dated Aug. 20, 2024, 18 pp.

International Preliminary Report on Patentability from International Application No. PCT/US2022/021481 dated Sep. 12, 2023, 6 pp.

Prosecution History from U.S. Appl. No. 29/831,830, now U.S. Pat. No. D1,006,248, dated Aug. 10, 2023 through Oct. 2, 2023, 18 pp.

International Search Report and Written Opinion for PCT/US2022/021481 mailed Jun. 6, 2022.

| | |
|---|---|
| 1<br>Bend your neck downward about 15-20 degrees | 2<br>Do NOT lean back until the process is completed |
| 3<br>Insert device into your nose and point it toward your ear | 4<br>Push firmly on the syringe plunger to wash your nose. Hold your breath during the washing process |
| 5<br>Keep the device against your nose for 10 seconds to allow complete drainage | 6<br>Remove the device from your nose, making sure to hold it upright. Insert the sealing cap |

7 Use the included shipping label to seal the test kit.

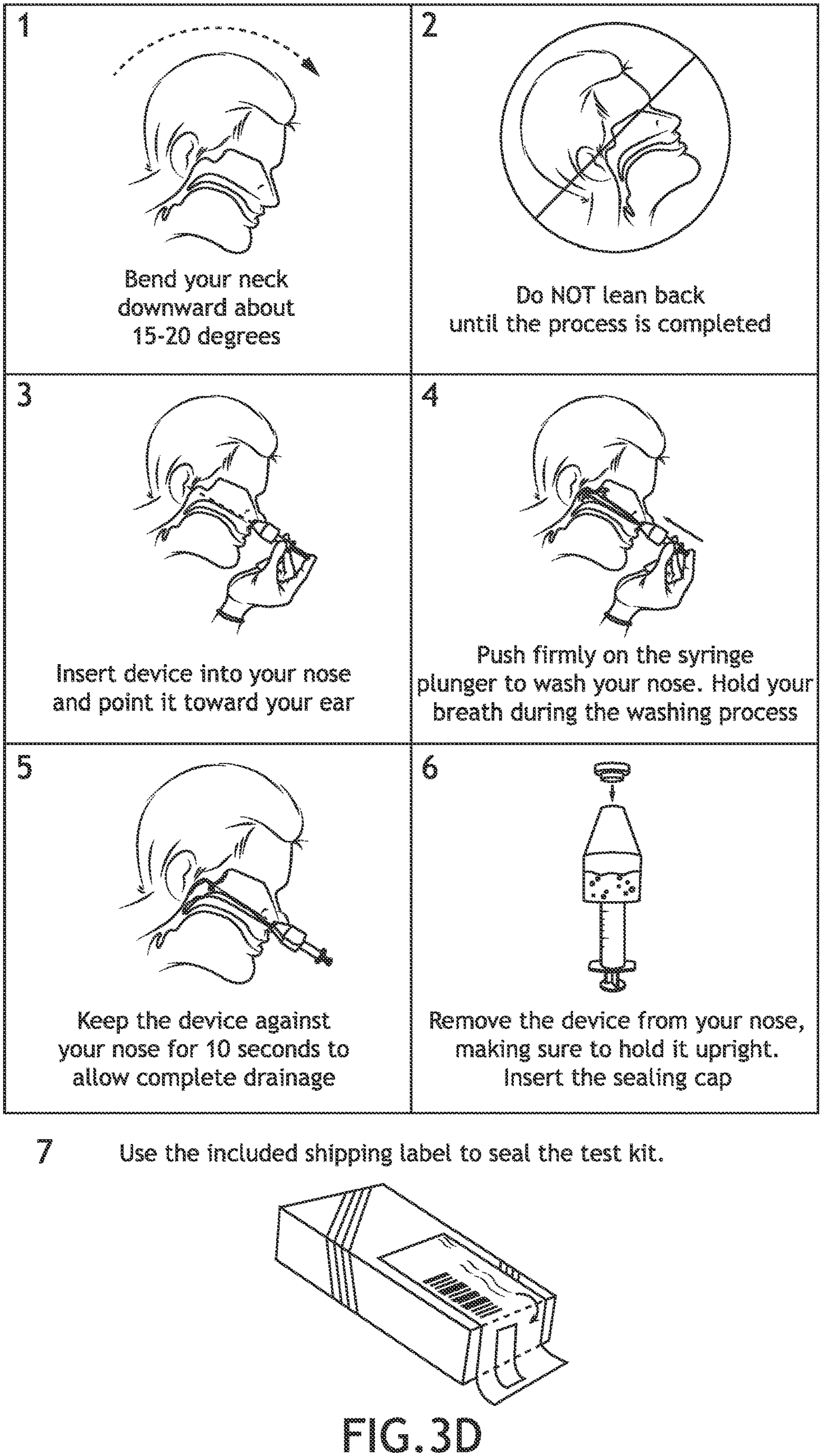

FIG.3D

NASAL SPECIMEN COLLECTION SYSTEM

CROSS-REFERENCE TO RELATED APPLICATIONS

The present application claims priority under 35 U.S.C. § 119(e) to U.S. Provisional Application Ser. No. 63/166,322, filed Mar. 26, 2021, and titled "Nasal Specimen Collection System," which is incorporated herein by reference in its entirety.

TECHNICAL FIELD

The present invention generally relates to apparatus, systems, or methods for collection of nasal specimens.

BACKGROUND

Widespread diagnostic testing for the SARS-CoV-2 virus continues to be a limiting factor in efforts to accurately project case numbers and contain the disease known as COVID-19. After the first confirmed case of COVID-19 in China, the virus quickly became the center of a global pandemic resulting in economic and social shutdowns. Global supply and personnel shortages stifled the deployment of testing options for patients, hindering downstream processes such as contact tracing and containment. This problem is further compounded by barriers that prevent patients from accessing testing resources. With the resurgence of endemic respiratory tract infections (RTI) such as influenza, it is paramount to have reliable alternative testing modalities to bolster the current infrastructure.

Since the beginning of the 2020 COVID-19 pandemic, there has been an influx of academic and corporate interest in developing alternative testing methods for RTI. The nasopharyngeal swab is the gold standard collection method for COVID-19, due to data suggesting a higher viral concentration in the nasopharyngeal cavity. However, the literature suggests lower patient acceptance of the nasopharyngeal swab collection method with procedural discomfort attributing to the low acceptance rate. This procedure is somewhat invasive and traumatizing for patients as it requires deep probing of the posterior nasopharynx with a stiff swab applicator. The nasopharyngeal swab procedure has been known to cause pain and injuries such as epistaxis. Additionally, there is also a considerable infection risk to healthcare workers administering the nasopharyngeal swab as patients tend to cough or sneeze during the procedure.

Given the state of the art, there is a need for alternative collection methods that are more comfortable but can produce adequate specimens when compared to a nasopharyngeal swab.

SUMMARY

An apparatus for collecting nasal specimens is disclosed. In embodiments, the apparatus includes a device body with a nozzle at a distal end of the device body. The nozzle is configured to interface with a nasal cavity. The apparatus further includes an irrigation path and a collection path within the device body. The collection path may be separate from the irrigation path. The irrigation path is configured to direct a fluid from an irrigation chamber into the nasal cavity in order to dislodge a sample from the nasal cavity. When the fluid flows back out of the nasal cavity, the collection path is configured to direct at least a portion of the fluid and the sample dislodged from the nasal cavity into a collection chamber.

In some embodiments, the apparatus is part of a system that includes an actuator (e.g., a syringe, bulb-type actuator, or the like) configured to drive the fluid through the irrigation path. The system may further include a cap configured to enclose the collection chamber when the cap is coupled to the nozzle. In this regard, a user may employ the system to collect a nasal specimen and secure it within the apparatus so that the specimen can be safely transported to a lab for examination.

A method of collecting a nasal specimen using the apparatus is also disclosed. The method includes at least the following steps: (1) interfacing the nozzle at the distal end of the device body with a nasal cavity; (2) directing fluid through the irrigation path into the nasal cavity in order to dislodge a sample from the nasal cavity; and (3) retrieving at least a portion of the fluid and the sample dislodged from the nasal cavity via the collection path.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

FIG. 3D is a more detailed view of the set of instructions illustrated in FIG. 3C, in accordance with one or more embodiments of this disclosure.

DETAILED DESCRIPTION

The present disclosure is directed to a nasal specimen collection (NSC) system that includes a NSC apparatus with an irrigation path and a collection path. The irrigation path is configured to direct fluid into a nasal cavity in order to dislodge a sample (also referred to herein as a "specimen") from the nasal cavity, and when the fluid flows back out of the nasal cavity, the collection path is configured to direct at least a portion of the fluid and the sample dislodged from the nasal cavity into a collection chamber.

In exploring a potential alternative nasopharyngeal specimen collection method, the inventors developed the concept of nasopharyngeal debridement using fluid irrigation. This alternative respiratory pathogen collection device (the NSC apparatus) was designed to be self-administered by the patient but can also be administered by a healthcare professional. The NSC apparatus irrigates the patient's nasopharyngeal cavity with a fluid (e.g., saline solution), debriding epithelial cells potentially harboring respiratory pathogens. The irrigation solution is immediately recaptured into a self-contained collection chamber within the NSC apparatus, minimizing the need to handle infectious bodily fluids. By the nature of a self-administered and self-contained device, there is considerably less infection risk for healthcare professionals. It is also contemplated that replacement of the traditional nasopharyngeal swab with a fluid debridement mechanic will make the procedure less invasive, resulting in higher patient acceptance.

Through the course of developing the NSC apparatus, the inventors determined that sufficient pathological sampling can be achieved by mechanism of nasopharyngeal irrigation that is proportionate to the nasopharyngeal swab method. Using data from wound care literature, it was determined an irrigation pressure of 5 to 15 PSI (pounds per square inch) would be sufficient to overcome the pathogen adhesion threshold. Taking this information into account, embodiments of the NSC apparatus described herein have been designed to apply an irrigation pressure of 5 to 20 PSI but not to exceed 30 PSI. However, the NSC apparatus may function appropriately at other irrigation pressures depending on the overall device structure and requirements of the application.

Figure 1A:
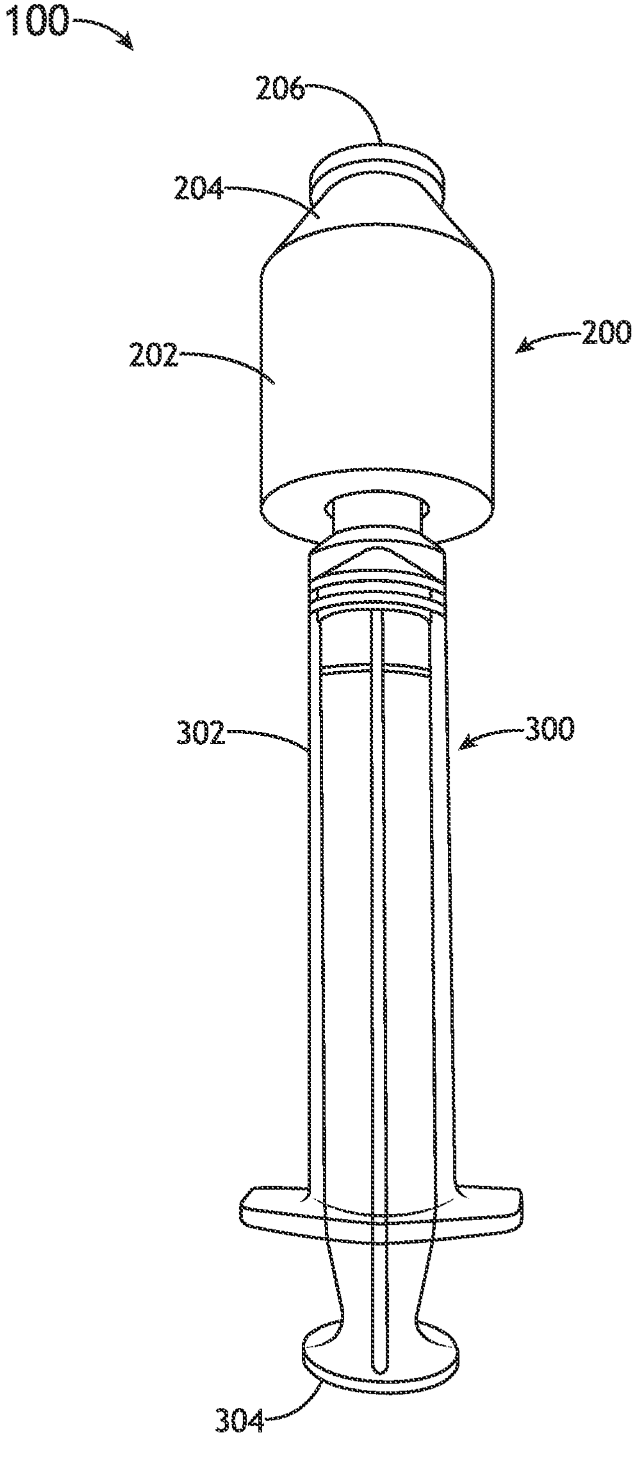
FIG. 1A is a birds-eye view of a nasal specimen collection (NSC) system, in accordance with one or more embodiments of this disclosure.
Figure 1B:
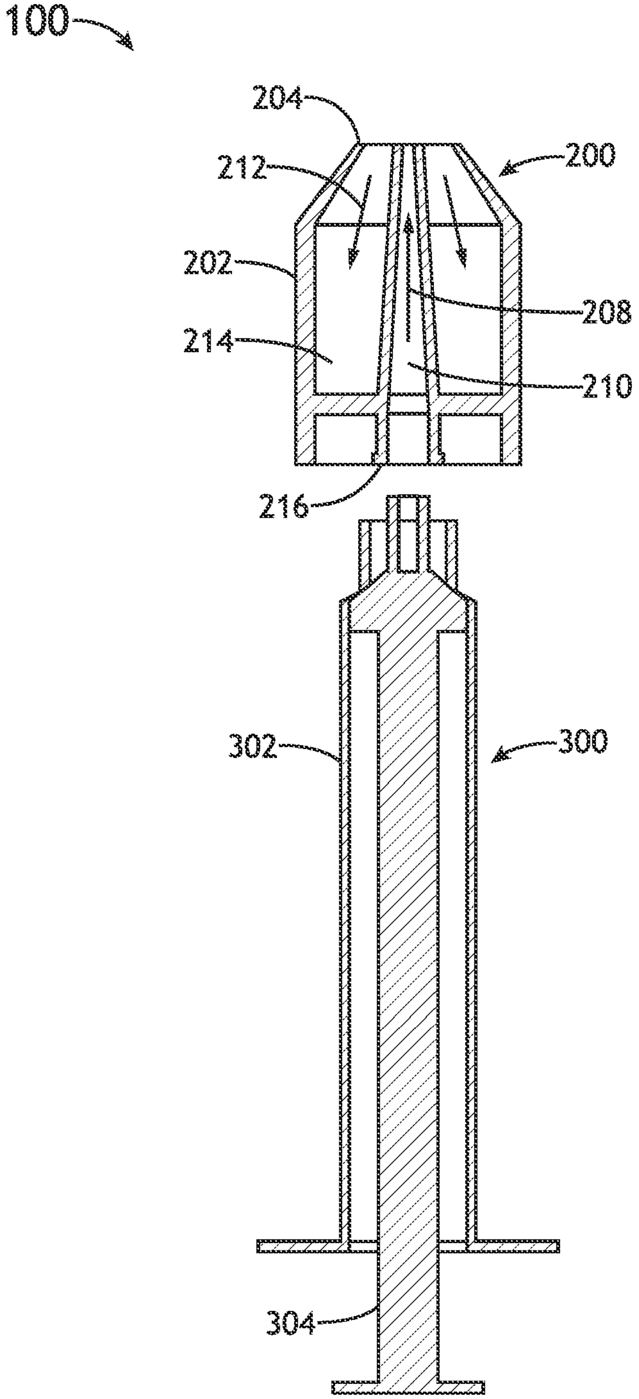
FIG. 1B is a cross-sectional partially exploded view of the NSC system of FIG. 1A, in accordance with one or more embodiments of this disclosure.

FIGS. 1A and 1B illustrate a NSC system 100, in accordance with one or more embodiments of the present disclosure. As shown in FIG. 1A, the NSC system 100 includes a NSC apparatus 200 and an actuator 300 configured to drive irrigation fluid through an irrigation path of the NSC apparatus 200.

In embodiments, the NSC apparatus 200 includes a device body 202 with a nozzle 204 at a distal end of the device body 202. The nozzle 204 is configured to interface with a nasal cavity. For example, the nozzle 204 may be tapered to fit into a nasal orifice and partially extend into the nasal cavity so that fluid can flow from the nozzle into a nasal passage and vice versa. In some embodiments, the nozzle 204 is at least partially conical. For example, the nozzle 204 in FIGS. 1A and 1B is shaped as a truncated cone. However, in other embodiments, the nozzle 204 may be shaped differently (e.g., in the shape of a dome, nested cylinders, tapered cylinder, angled/slanted cone, etc.).

As shown in FIG. 1B, an irrigation path 208 and a collection path 212 are defined within the device body 202. In some embodiments, the collection path 212 is separate from the irrigation path 208. The irrigation path 208 is configured to direct a fluid (e.g., saline solution) from an irrigation chamber 210 into the nasal cavity in order to dislodge a sample (e.g., epithelial cells or other specimen) from the nasal cavity. When the fluid flows back out of the nasal cavity, the collection path 212 is configured to direct at least a portion of the fluid and the sample dislodged from the nasal cavity into a collection chamber 214. In some embodiments, the collection chamber 214 contains a specimen preservation agent and/or a testing agent. For example, the collection chamber 214 may be prefilled with viral transport media (VTM) and/or an antigen detection agent.

The NSC system 100/apparatus 200 may further include a cap 206 configured to enclose the collection chamber 214 when the cap is coupled to the nozzle 204. For example, the cap 206 may cover or plug one or more distal openings of the NSC apparatus 200, thereby enclosing the collection chamber 214, when the cap is coupled to the tip of the nozzle 204. One embodiment of the cap 206 uses a friction mechanism in the form of a tapered plug to securely enclose fluid within the collection camber 214 and prevent leaking. In other embodiments, the cap 206 may use a threaded coupling interface, a force-fit or snap-fit connection, or any other fastening interface to seal a collected sample within the NSC apparatus 200. In this regard, a user may employ the NSC system 100 to collect a nasal specimen and secure it within the NSC apparatus 200 using the cap 206 to seal the specimen within the collection chamber 214 so that the specimen can be safely stored and/or transported to a laboratory, examination/research facility, or the like.

In some embodiments, the cap 206 is further configured to enclose the irrigation chamber 210 and may also be configured to isolate the irrigation chamber 210 from the collection chamber 214 in order to prevent fluid from leaking from one chamber into the other after a sample is collected and enclosed within the NSC apparatus 200 for storage and/or transport.

As shown in FIG. 1B, the NSC apparatus 200 may include a connector 216 at a proximal end of the device body 202 of the NSC apparatus 200. The connector 216 may be configured to couple the irrigation chamber 210 with the actuator 300 so that the actuator 300 can push fluid from the irrigation chamber 210 through the irrigation path 208 into the nasal cavity of the user.

In some embodiments, the actuator 300 is a syringe including a syringe barrel 302 and a plunger 304 configured to drive fluid through the syringe barrel 302. To accommodate a syringe connection, the connector 216 may be a luer lock or luer slip connector, or the like. The syringe barrel 302 may be preloaded with the fluid (e.g., saline solution) such that the fluid is transferred from the syringe barrel 302 to the irrigation chamber 210 and then pushed through the irrigation path 208. Alternatively, the fluid may be preloaded in the irrigation chamber 210, and the syringe barrel 302 may be filled with air or another fluid that is used to push the fluid from the irrigation chamber 210 through the irrigation path 208.

In other embodiments, the actuator 300 may be a bulb type actuator (e.g., saline bulb), a pump, or any other fluid actuator. Much like the syringe actuator embodiments described above, any other type of actuator may be loaded with the irrigation fluid and/or another fluid for driving the irrigation fluid through the irrigation path 208. Other actuator types may also use a luer lock, luer slip, or similar connection interface.

FIGS. 2A through 2F show more detailed views of the NSC apparatus 200, including a front perspective view (FIG. 2A), a rear perspective view (FIG. 2B), right side elevation view (FIG. 2C), a front elevation or distal end view (FIG. 2D), a right side cross-sectional view (FIG. 2E), and a front perspective cross-sectional view (FIG. 2F) of the NSC apparatus 200, in accordance with one or more embodiments of this disclosure.

Figure 2A:
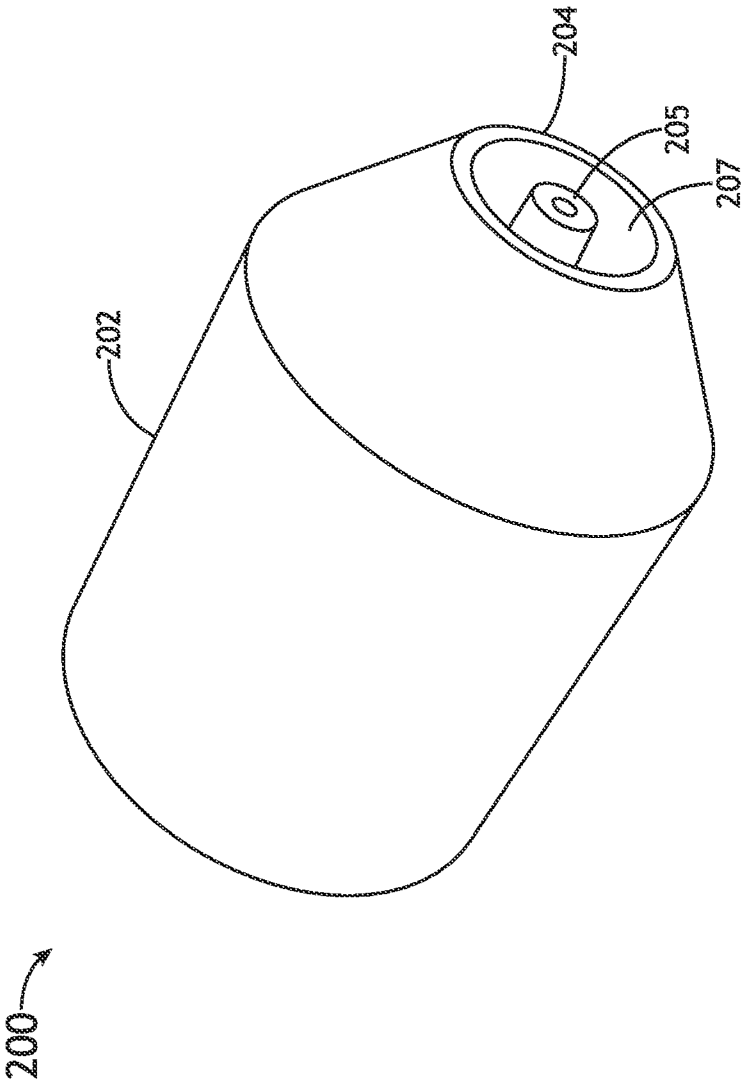
FIG. 2A is a front perspective view of a NSC apparatus of the NSC system of FIG. 1A, in accordance with one or more embodiments of this disclosure.

As shown in FIG. 2A, the tip of the nozzle 204 may have separate openings 205 and 207 for the irrigation path 208 and the collection path 212, respectively. In FIG. 2A, the openings 205 and 207 are shown as being circular and annular, respectively; however, in other embodiments, the nozzle 204 may have a different number of openings 205 for the irrigation path 208, a different number of openings 207 for the irrigation path 212, and/or a different arrangement of the openings 205 and 207.

In some embodiments, the irrigation path 208 and the collection 214 are coaxial. For example, FIG. 2D is a distal end view of the NSC apparatus 200 showing how the opening 205 for the irrigation path 208 is centered and surrounded by the opening 207 for the collection path 212. Furthermore, a cross-sectional view of the NSC apparatus 200 is provided in FIG. 2E, where it is shown that the irrigation path 208 and chamber 210 are centrally disposed within the device body 202 and surrounded by the collection path 212 and chamber 214. The irrigation path 208 and the collection path 212 may be defined by an inner lumen that is connected to (or is a part of) chamber 210 and an outer lumen that is connected to (or is a part of) chamber 214. However, in other embodiments, the irrigation path 208 and the collection path 212 may be arranged differently (e.g., reversed or arranged side-by-side, one only partially surrounding the other, and so forth).

The device body 202 may be cylindrical. Alternatively, the device body 202 can be tapered (e.g., at least partially conical), dome shaped, barrel shaped, bulbous, or any other shape suitable for containing the irrigation path 208 and collection path 212. The irrigation chamber 210 and the collection chamber 214 may also be disposed within the device body 202. However, in other embodiments, the irrigation chamber 210 and the collection chamber 214 may only be partially disposed within the device body 202, externally coupled to the irrigation/collection paths, and/or arranged differently (e.g., reversed or arranged side-by-side, one in front of the other, one only partially surrounding the other, and so forth).

Figure 2B:
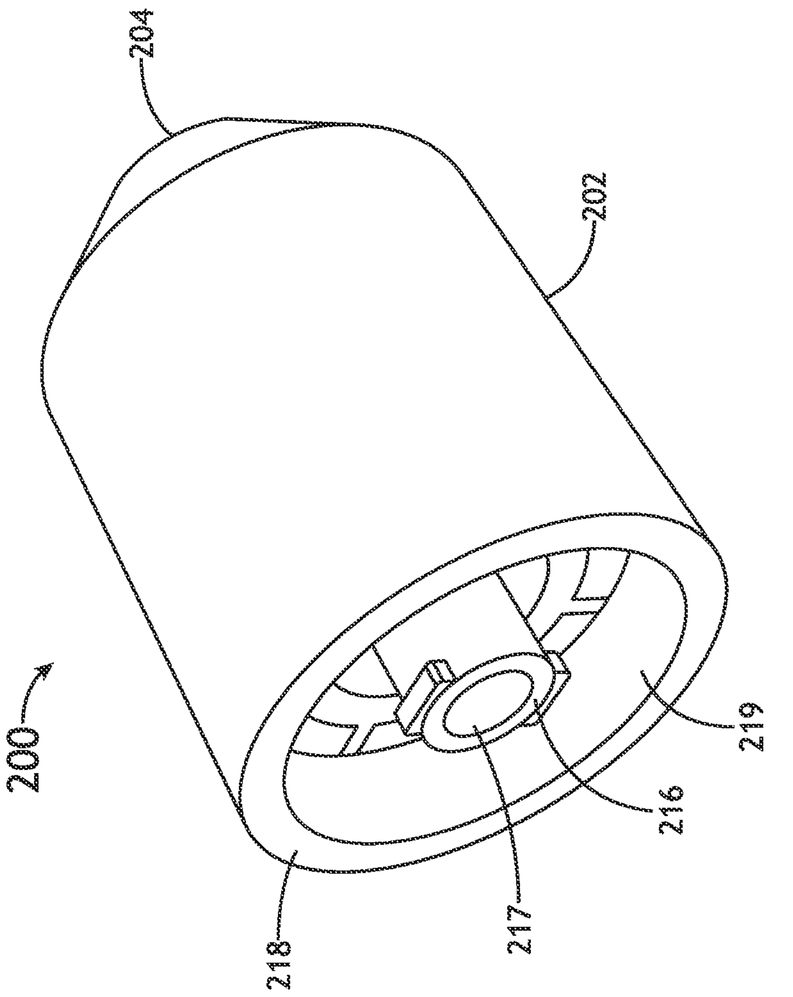
FIG. 2B is a rear perspective view of the NSC apparatus of the NSC system of FIG. 1A, in accordance with one or more embodiments of this disclosure.
Figure 2C:
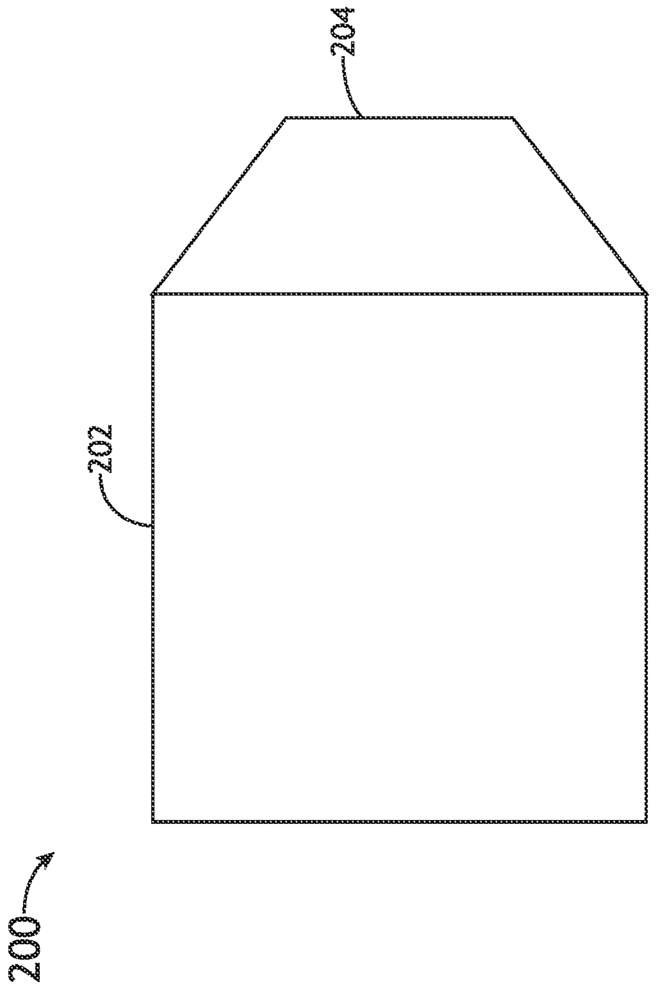
FIG. 2C is a right side elevation view of the NSC apparatus of the NSC system of FIG. 1A, in accordance with one or more embodiments of this disclosure.
Figure 2D:
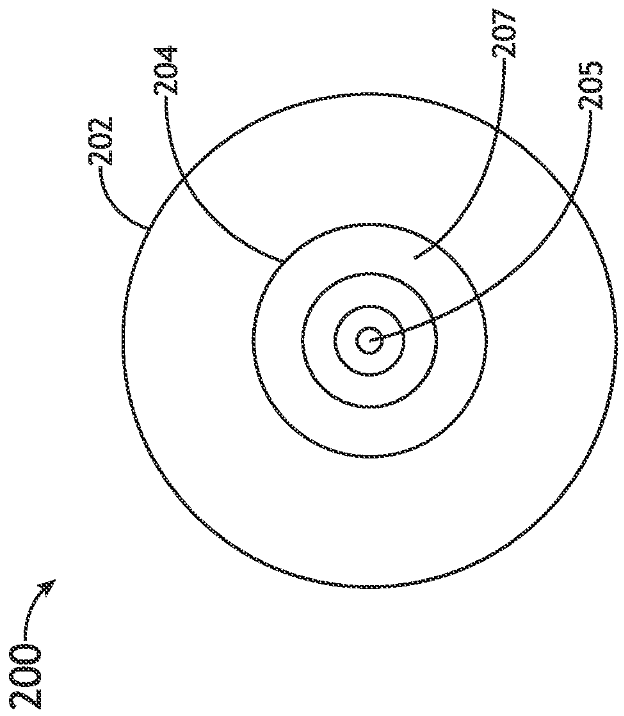
FIG. 2D is a front elevation view of the NSC apparatus of the NSC system of FIG. 1A, in accordance with one or more embodiments of this disclosure.
Figure 2E:
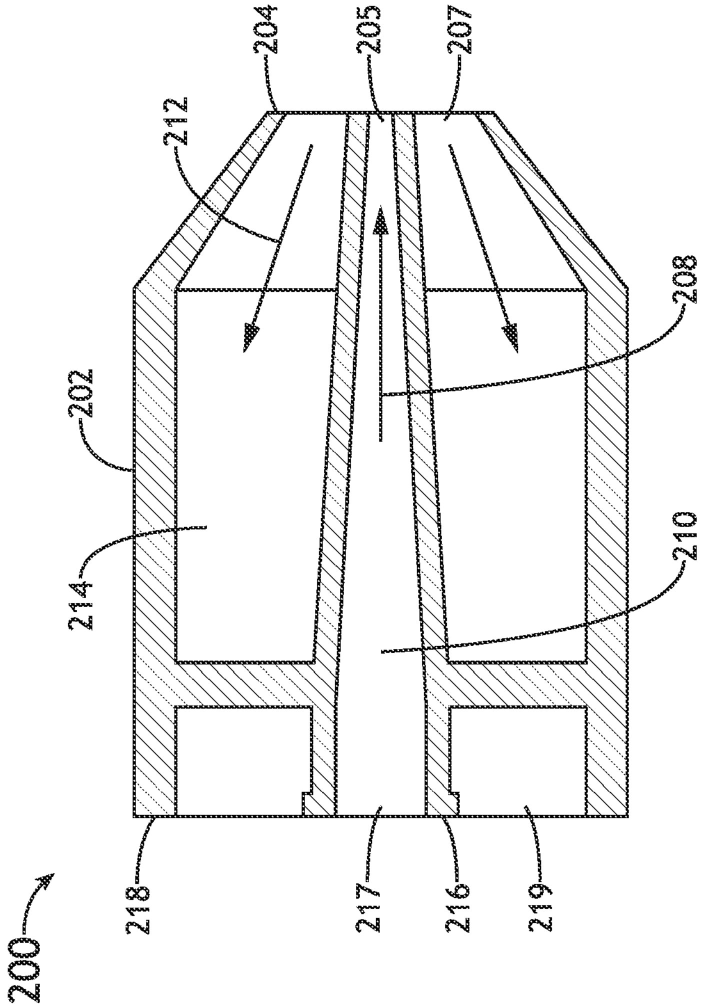
FIG. 2E is a right side cross-sectional view of the NSC apparatus of the NSC system of FIG. 1A, in accordance with one or more embodiments of this disclosure.
Figure 2F:
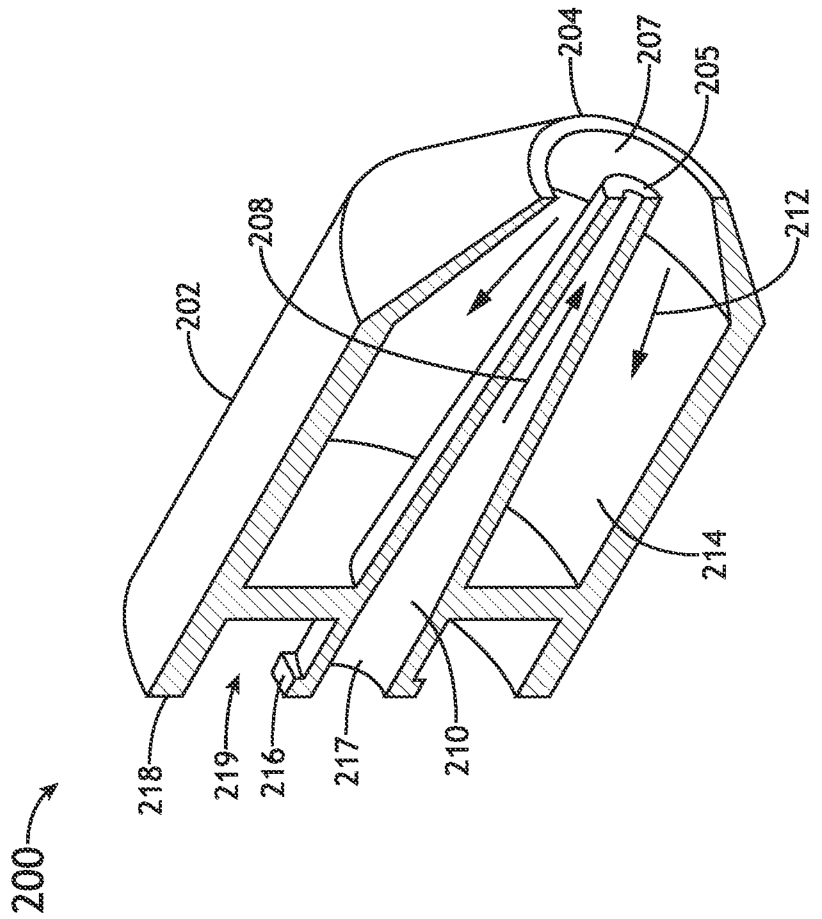
FIG. 2F is a front perspective cross-sectional view of the NSC apparatus of the NSC system of FIG. 1A, in accordance with one or more embodiments of this disclosure.

As shown in FIG. 2B, the rear/proximal end of the NSC apparatus 200 includes a port 217 for connecting the actuator 300 to the irrigation chamber 210 (or directly to the irrigation path 208 in some embodiments). The connector 216 may facilitate a secure coupling between the actuator 300 and the port 217. In some embodiments, the rear/proximal end of the NSC apparatus 200 may also have an outer ridge 218 that defines a cavity/indentation 219 configured to receive a distal end of the actuator 300 for a more secure fit or coupling between the two components. Cross-sectional views in FIGS. 2E and 2F further illustrate the actuator connection interface at the rear/proximal end of the NSC apparatus 200, in accordance with one or more embodiments of this disclosure.

In some embodiments, the NSC apparatus 200 is formed by a single mold/print. For example, the NSC apparatus 200 may be entirely formed by a continuous 3D printed structure. Alternatively, portions of the NSC apparatus 200 may be separately printed or cast and then assembled together. For example, the nozzle 204 may be printed or cast separately from the device body 202, the inner lumen (e.g., irrigation chamber 210) may be printed or cast separately from the outer lumen (e.g., collection chamber 214), and so forth. Separately manufacturing portions of the NSC apparatus 200 may have advantages for injection molding processes because simpler molds and/or less material can be utilized. In particular, the tip of the nozzle 204 that forms a portion of the outer lumen for the collection path 212 may be separately manufactured from the device body 202. Meanwhile, the inner lumen for the irrigation path 208 and/or chamber 210 may be printed or cast with the device body 202. Alternatively, all three portions (the tip of the nozzle 204, the inner lumen, and the device body 202) may be separately manufactured.

Figure 3A:
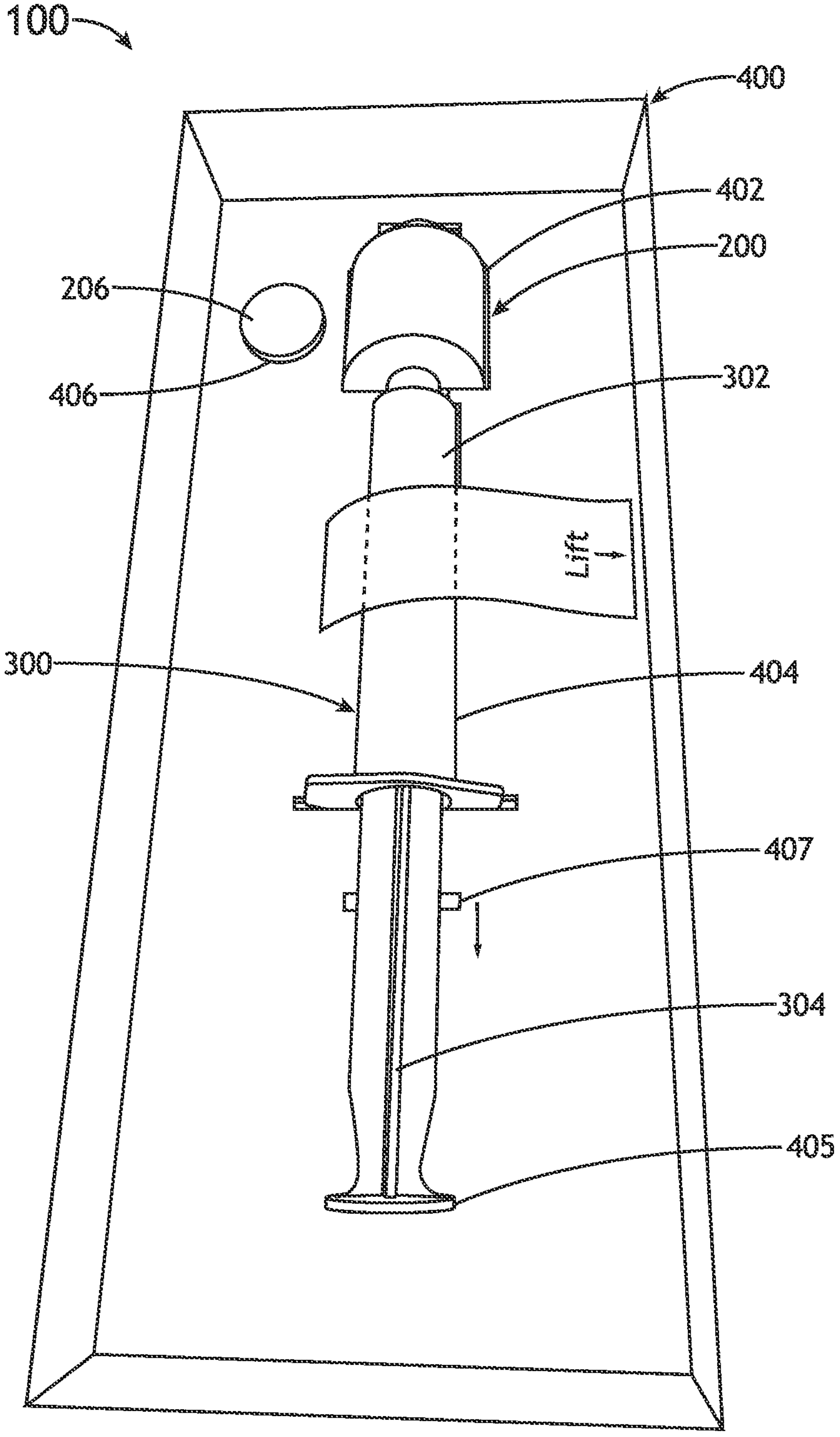
FIG. 3A is a birds-eye view of the NSC system of FIG. 1A including an enclosure for the system, wherein various system components are disposed within distinct cutouts formed in the enclosure, in accordance with one or more embodiments of this disclosure.
Figure 3B:
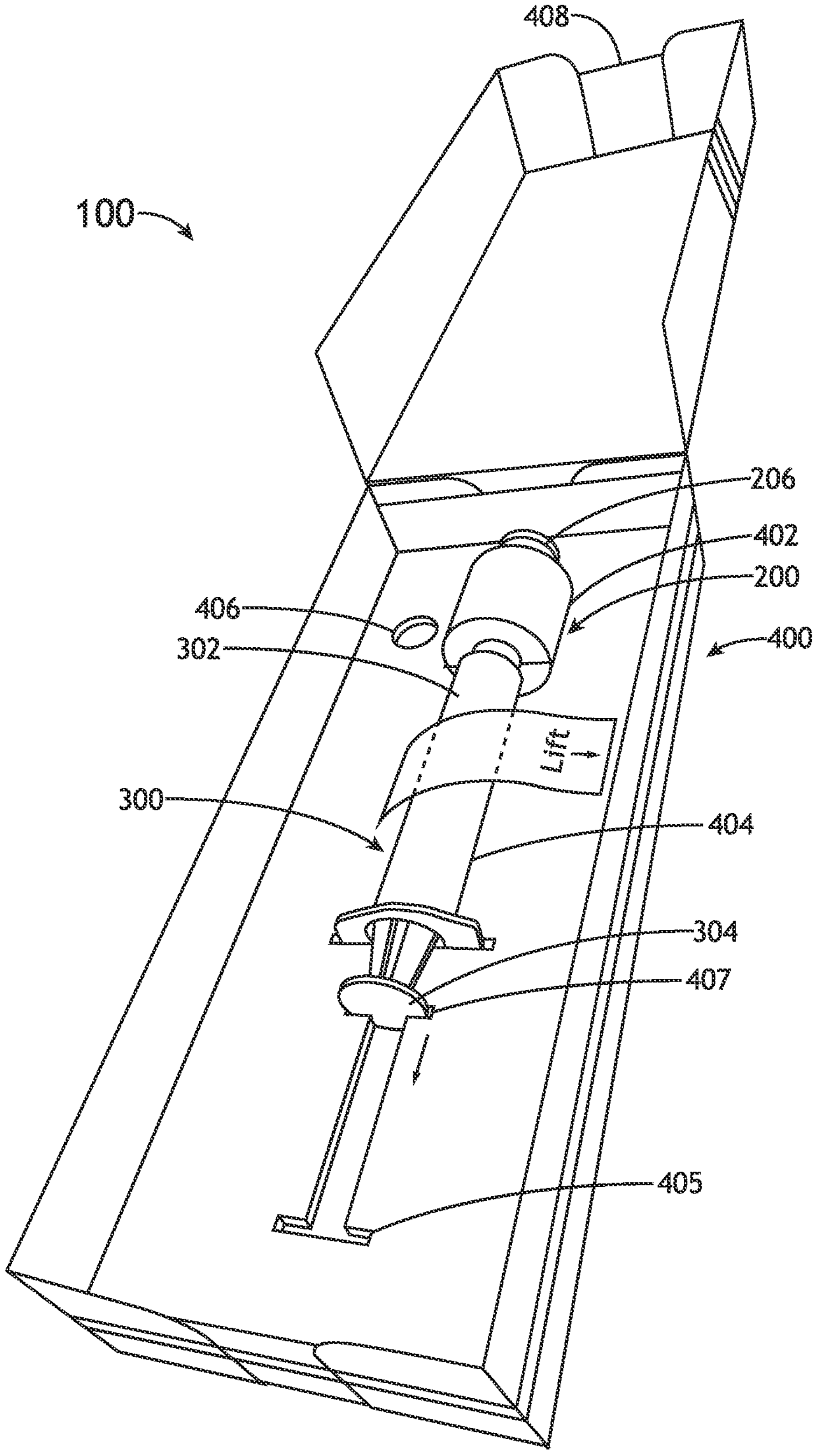
FIG. 3B is a perspective view of the NSC system of FIG. 3A, in accordance with one or more embodiments of this disclosure.

Referring now to FIGS. 3A and 3B, the NSC system 100 may be packaged as a kit in some embodiments. For example, the NSC system 100 may include a portable enclosure 400 with distinct cutouts 402, 404, and 406 configured to hold the NSC apparatus 200, the actuator 300, and the cap 206, respectively. The cutouts 402, 404, and 406 may have specific sizes and shapes to fit each of the respective components within the cutouts so that they are secured within the portable enclosure 400. In some embodiments, these can be cardboard or foam cutouts. Alternatively, the cutouts 402, 404, and 406 may be defined by indentations in one or more plastic inserts (e.g., ABS, PMMA, PETG, HIPS, polycarbonate, polypropylene, polyethylene, etc.). In this regard, the term "cutout" may include any type of cavity formed in a substrate configured to hold one or more components of the NSC system 100. Furthermore, the cutout 404 for the actuator 300 may include sub-cutouts 405 and 407 to accommodate multiple positions (e.g., depressed and undepressed positions) of a movable member of the actuator 300 (e.g., the syringe plunger 304).

FIG. 3A illustrates the NSC system 100 prior to use, where the NSC apparatus 200, the actuator 300, and the cap 206 are all disposed within respective cutouts 402, 404, 406 of the portable enclosure 400, and the moveable member (syringe plunger 304) of the actuator 300 is in an initial (undepressed) position at sub-cutout 405. The NSC apparatus 200 and actuator 300 can be removed from the portable enclosure 400 and used to collect a sample. The NSC apparatus 200 may then be sealed with the cap 206 to secure the sample within the collection chamber 214 of the NSC apparatus 200. As shown in FIG. 3B, the sealed NSC apparatus 200 and actuator 300 can be placed back into the respective cutouts 402 and 404 for the NSC apparatus 200 and actuator 300 with the moveable member (syringe plunger 304) of the actuator 300 in a final (depressed) position at sub-cutout 407.

Figure 3C:
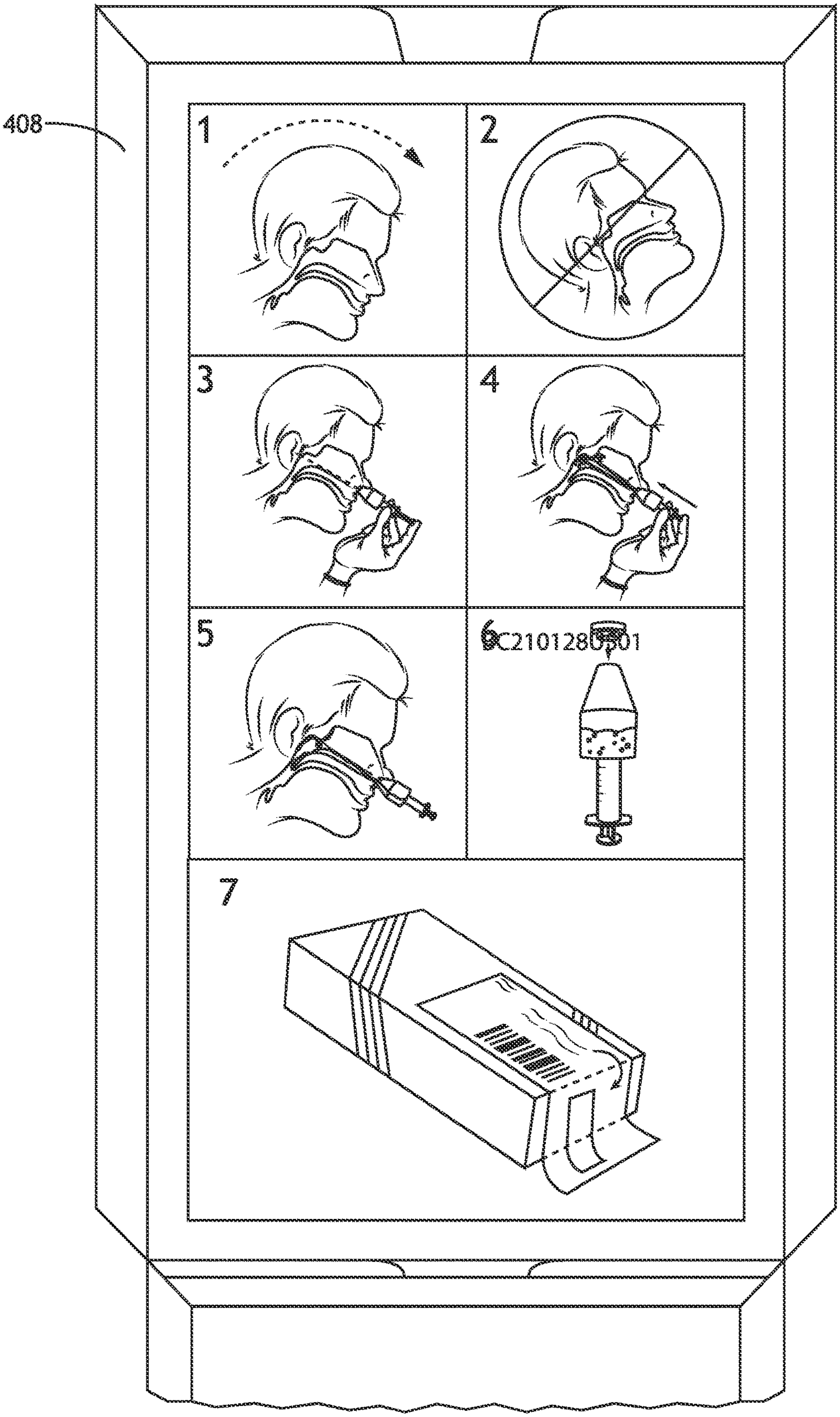
FIG. 3C illustrates an inner surface of a lid of the enclosure of the NSC system of FIG. 3A, wherein a set of instructions for using the system is printed or adhered to the inner surface of the lid, in accordance with one or more embodiments of this disclosure.

In embodiments, the portable enclosure 400 includes a lid 408 configured to secure the NSC system 100 components within the portable enclosure 400. For example, FIG. 3B illustrates the lid 408 as a clamshell lid; however, the lid may be a standard box lid, flap, or any other type of lid. As shown in FIG. 3C, the lid 408 may have a set of instructions printed or adhered to an inner surface of the lid 408. Alternatively, the instructions may be printed on a separate paper/card within the portable enclosure 400 or disposed on a different surface (e.g., top, bottom, or side) of the portable enclosure 400.

As shown in FIG. 3D, an example set of instructions for a self-administered test may include but is not limited to the following steps: (1) Bend your neck downward about 15-20 degrees; (2) Do not lean back until the process is completed; (3) Insert device into your nose and point it toward your ear; (4) Push firmly on the syringe plunger to wash your nose. Hold your breath during the washing process; (5) Keep the device against your nose for 10 seconds to allow complete drainage; (6) Remove the device from your nose, making sure to hold it upright. Insert the sealing cap; and (7) Use the included shipping label to seal the test kit.

More generally, a method of using the NSC system 100, whether self-administered or administered by another person (e.g., a healthcare professional), includes at least the following steps: (1) interfacing the nozzle 204 at the distal end of the device body 202 with a nasal cavity; (2) directing fluid through the irrigation path 208 into the nasal cavity in order to dislodge a sample from the nasal cavity; and (3) retrieving at least a portion of the fluid and the sample dislodged from the nasal cavity via the collection path 212. Additionally, the method may include one or more steps described in relation to or inherently necessitated by any of the embodiments of the NSC system 100 or its components (e.g., NSC apparatus 200 and/or actuator 300) described herein.

FIGS. 4 through 17 illustrate various alternative embodiments of the NSC system 100 and/or its components (e.g., NSC apparatus 200 and/or actuator 300). Any of the embodiments described herein may be combined to achieve additional embodiments of the NSC system 100. For example, the NSC apparatus 200 (or a portion thereof) described in relation to one embodiment of this disclosure may replace the NSC apparatus 200 (or a portion thereof) described in relation to another embodiment of this disclosure. Similarly, the actuator 300 (or a portion thereof) described in relation to one embodiment of this disclosure may replace the actuator 300 (or a portion thereof) described in relation to another embodiment of this disclosure. Furthermore, any embodiment of the NSC apparatus 200 may be combined with any embodiment of the actuator 300. Any of the foregoing combinations/modifications are included in the scope of this disclosure unless otherwise specified in the claims.

Figure 4:
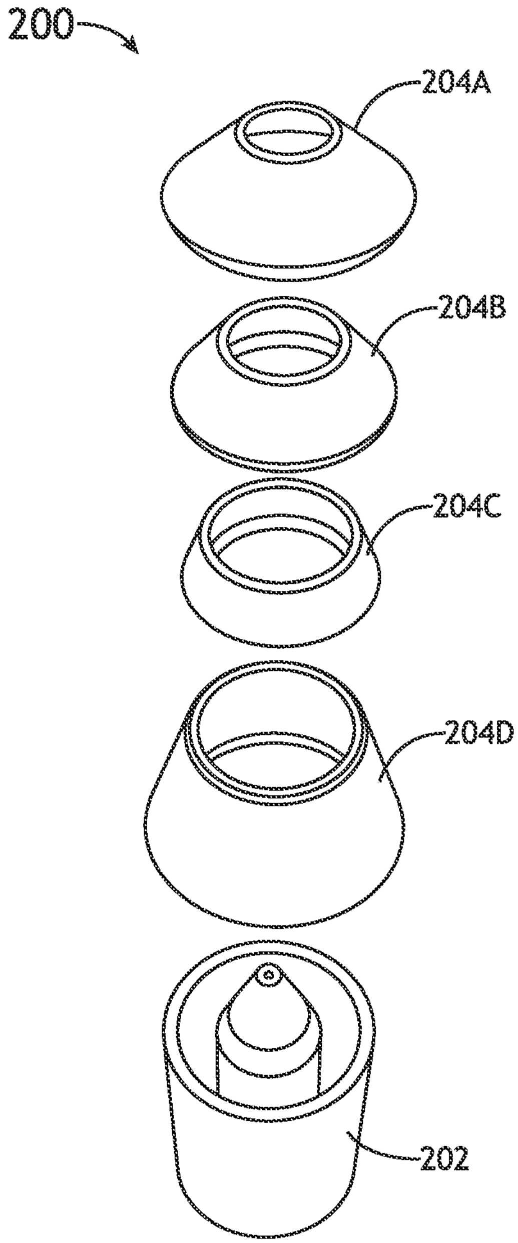
FIG. 4 is an exploded view of the NSC apparatus of the NSC system, in accordance with one or more alternative embodiments of this disclosure.

As shown in FIG. 4, in some embodiments, the NSC apparatus 200 includes a plurality of nozzle tips (e.g., nozzle tips 204A-204D) that can be coupled to the distal end of the device body 202 and/or stacked on top of one another to accommodate differently sized/shaped nasal orifices. For example, the nozzle tips may include a small nozzle tip 204A, medium nozzle tip 204B, large nozzle tip 204C, and extra-large nozzle tip 204D. The foregoing set of nozzle tips is provided as an example, but in other embodiments, the NSC apparatus 200 may include a different number of nozzle tips to choose from and/or different shapes.

Figure 5:
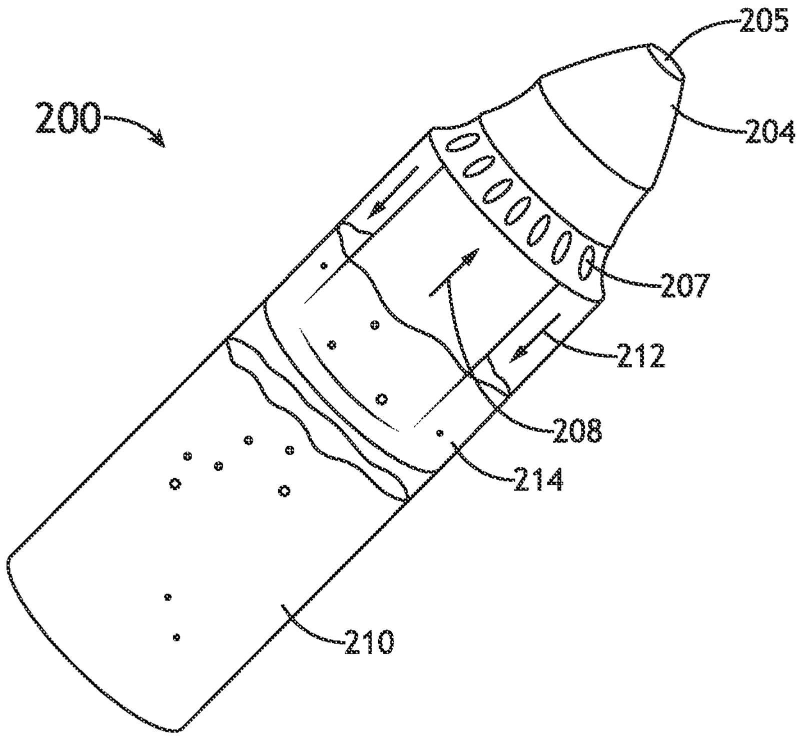
FIG. 5 is a perspective view of the NSC apparatus of the NSC system, in accordance with one or more alternative embodiments of this disclosure.

FIG. 5 illustrates an alternative embodiment of the NSC system 100/NSC apparatus 200 where the irrigation chamber 210 is larger and located behind the collection chamber 214. In the embodiment illustrated in FIG. 5B, the nozzle 204 has a distal opening 205 for the irrigation path 208 and a plurality of openings 207 encircling the base of the nozzle 204 for the collection path 212. In some embodiments, the irrigation chamber 210 may be surrounded by a flexible or at least somewhat deformable membrane so that fluid from the irrigation chamber 210 can be actuated by squeezing the membrane (like a squirt bottle or bladder) to drive the fluid through the irrigation path 208.

Figure 6A:
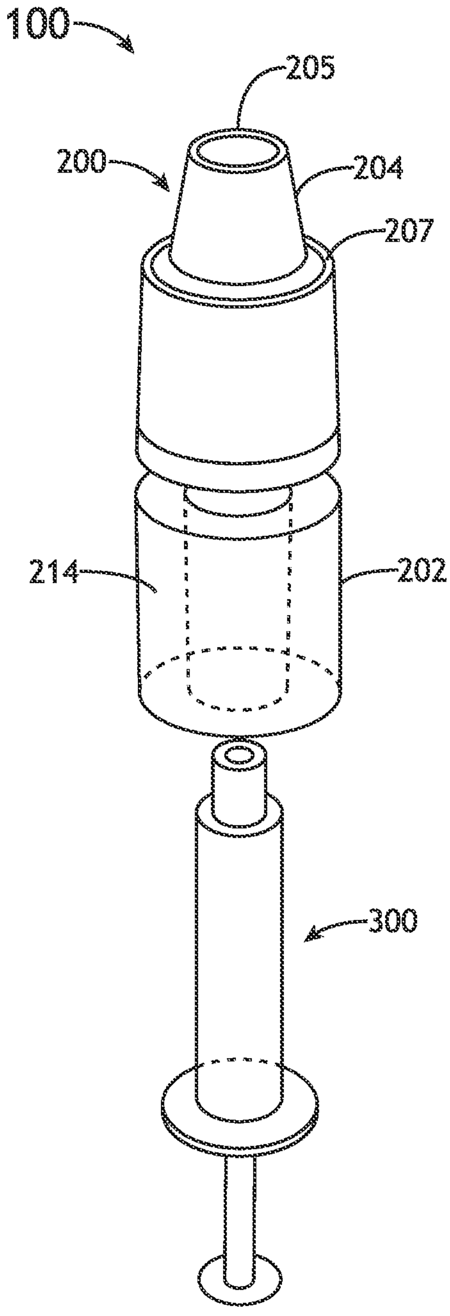
FIG. 6A is a partially exploded view of the NSC system, in accordance with one or more alternative embodiments of this disclosure.
Figure 6B:
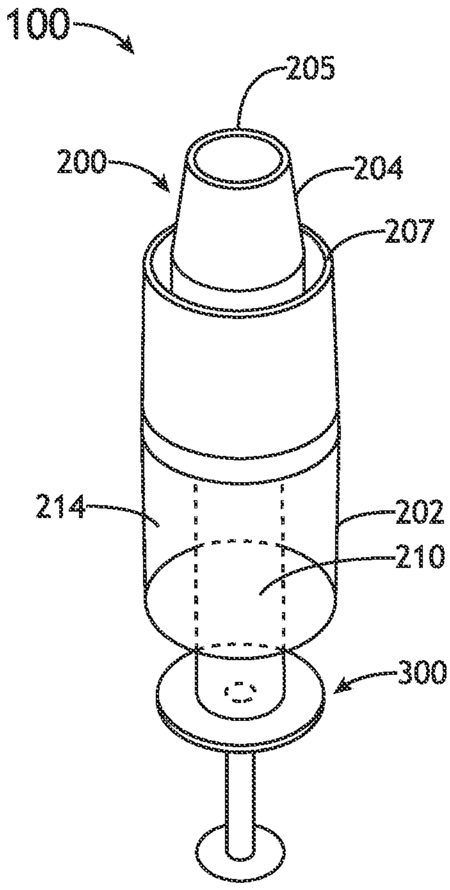
FIG. 6B is a perspective view of the NSC system of FIG. 6A, in accordance with one or more alternative embodiments of this disclosure.
Figure 6C:
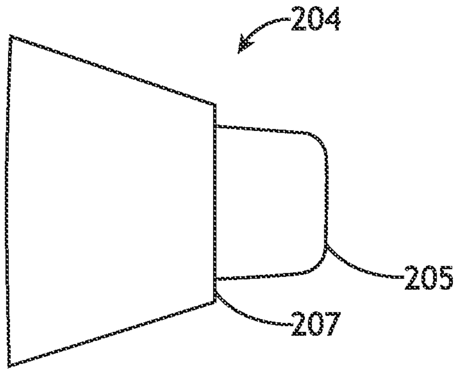
FIG. 6C is a right side elevation view of a nozzle of the NSC apparatus of the NSC system of FIG. 6A, in accordance with one or more alternative embodiments of this disclosure.
Figure 6D:
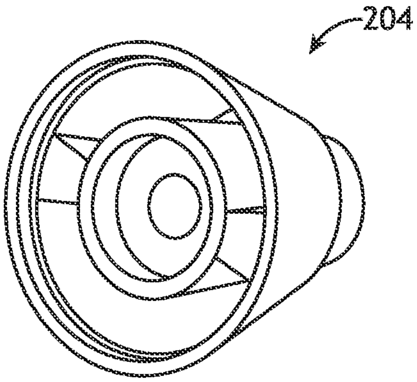
FIG. 6D is a rear perspective view of the nozzle of the NSC apparatus of the NSC system of FIG. 6A, in accordance with one or more alternative embodiments of this disclosure.
Figure 6E:
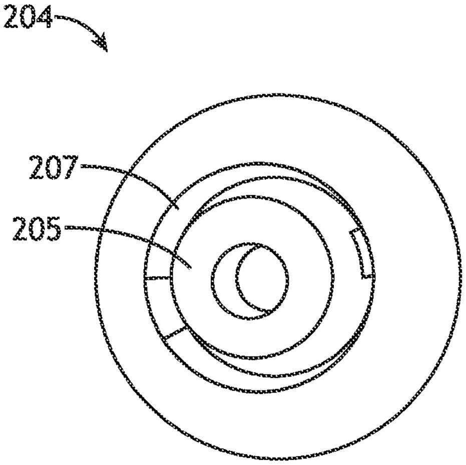
FIG. 6E is a front perspective view of the nozzle of the NSC apparatus of the NSC system of FIG. 6A, in accordance with one or more alternative embodiments of this disclosure.
Figure 6F:
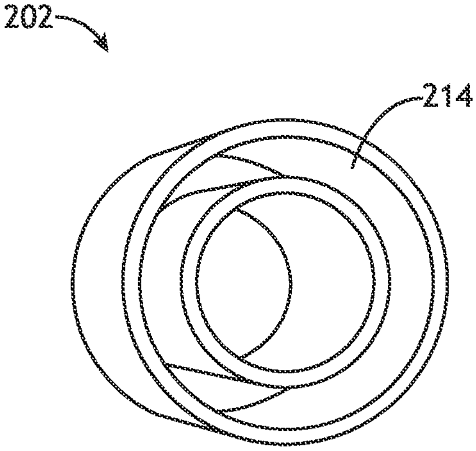
FIG. 6F is a front perspective view of a collection chamber of the NSC apparatus of the NSC system of FIG. 6A, in accordance with one or more alternative embodiments of this disclosure.

FIGS. 6A through 6F illustrate an alternative embodiment of the NSC system 100/NSC apparatus 200 where the nozzle 204 includes a distal opening 205 for the irrigation path 208 and an annular opening 207 encircling the base of the nozzle 204 for the collection path 212. In this embodiment, the device body 202 includes the collection chamber 214 encircling a cylindrical cavity that is configured to receive a syringe (i.e., the actuator 300). As shown in FIG. 6B, the syringe barrel then acts as the irrigation chamber 210. FIGS. 6C through 6E show more detailed views of the nozzle 204 as illustrated in FIGS. 6A and 6B, and FIG. 6F shows a more detailed view of the device body 202.

Figure 7:
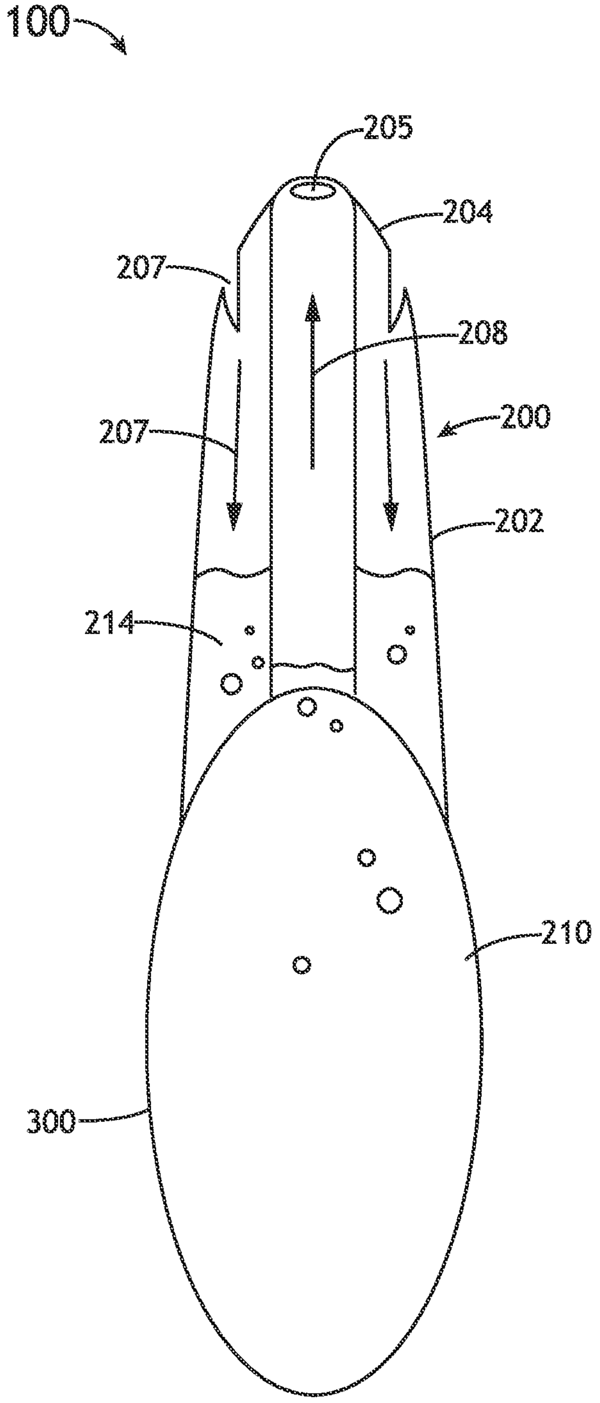
FIG. 7 is a schematic illustration of the NSC system, in accordance with one or more alternative embodiments of this disclosure.

FIG. 7 illustrates an alternative embodiment of the NSC system 100/NSC apparatus 200 where the actuator 300 is a bulb-type actuator (e.g., a saline bulb). In FIG. 7, the bulb also acts as the irrigation chamber 210. Alternatively, the bulb may be filled with another fluid (e.g., air or liquid) that drives the irrigation fluid through an irrigation chamber 210 in the device body 202 of the NSC apparatus 200.

Figure 8:
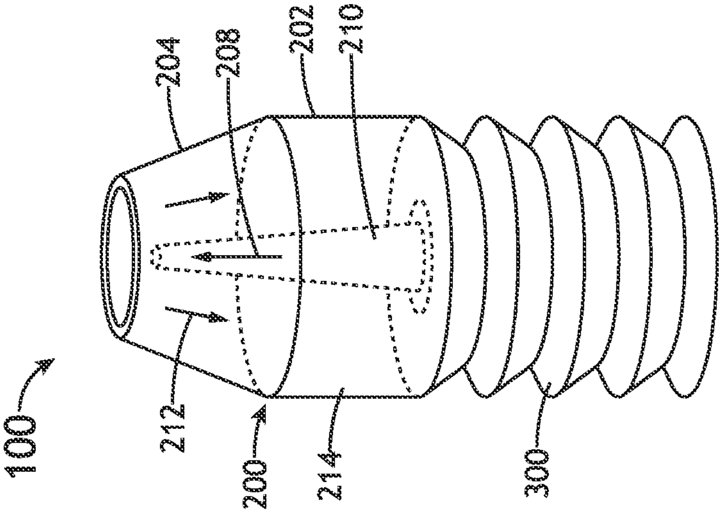
FIG. 8 is a schematic illustration of the NSC system, in accordance with one or more alternative embodiments of this disclosure.

FIG. 8 illustrates an alternative embodiment of the NSC system 100/NSC apparatus 200 where the actuator 300 is a compressible accordion style bladder. In some embodiments, the bladder is pre-attached to the NSC apparatus 200. The bladder may also act as the irrigation chamber 210. Alternatively, the bladder may be filled with another fluid (e.g., air or liquid) that drives the irrigation fluid through an irrigation chamber 210 in the device body 202 of the NSC apparatus 200. The bladder may be compressed by applying upward pressure, similar to the mechanism for actuating a syringe plunger.

Figure 9:
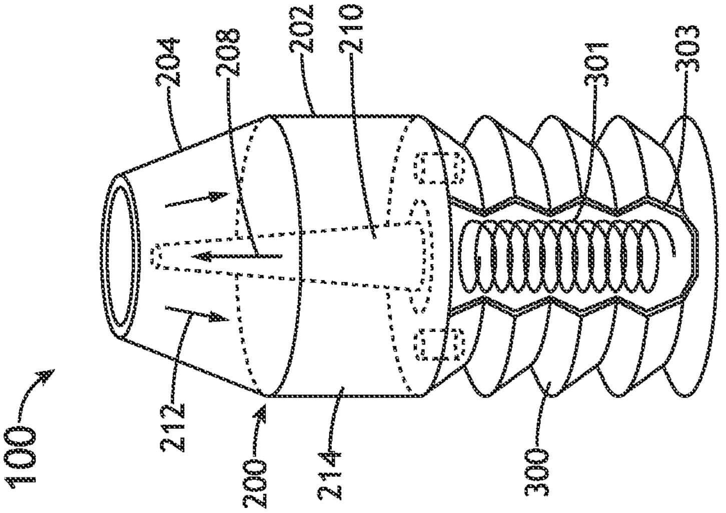
FIG. 9 is a schematic illustration of the NSC system, in accordance with one or more alternative embodiments of this disclosure.

FIG. 9 illustrates an alternative embodiment of the NSC system 100/NSC apparatus 200 where the actuator 300 is a compressible accordion style bladder similar to the actuator 300 in FIG. 8; however the bladder in FIG. 9 further includes a spring 301 inside of the bladder that automatically reinflates the bladder when the user stops applying upward pressure. Reinflation of the bladder may generate a negative pressure within the collection chamber 214 to facilitate suction of the irrigation fluid, sample, contaminates, foreign bodies, etc. In some embodiments, the actuator 300 includes a membrane 303 around the spring 301 to maintain separation between the irrigation path 208 and the collection path 212.

Figure 10:
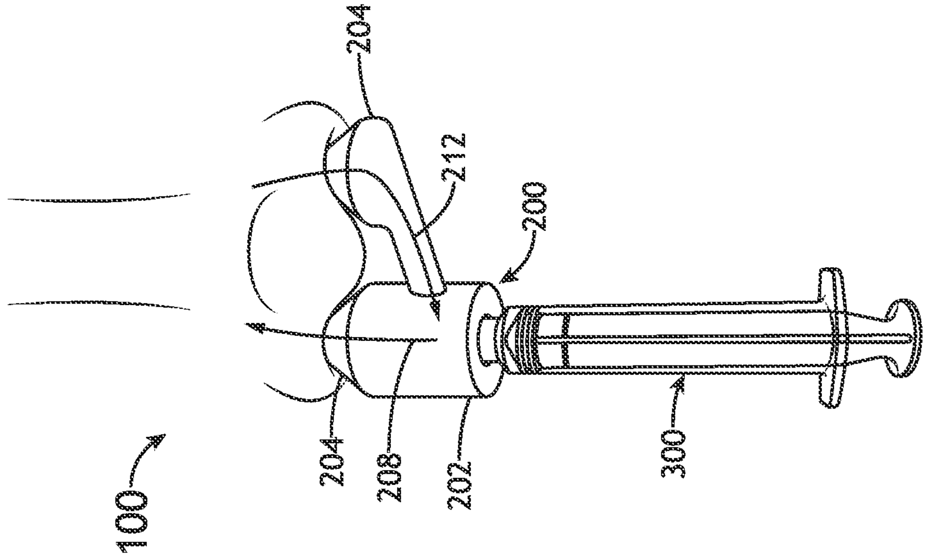
FIG. 10 is a schematic illustration of the NSC system, in accordance with one or more alternative embodiments of this disclosure.

FIG. 10 illustrates an alternative embodiment of the NSC system 100/NSC apparatus 200 with two nozzles 204 configured in a dual nostril design, where one nozzle 204 is connected to the irrigation path 208 and configured to irrigate one nozzle, and the other nozzle 204 is connected to the collection path 212 and used to collect any contralateral drainage from the other nostril. This design may be beneficial in children or patients who may not be able to follow instructions.

Figure 11:
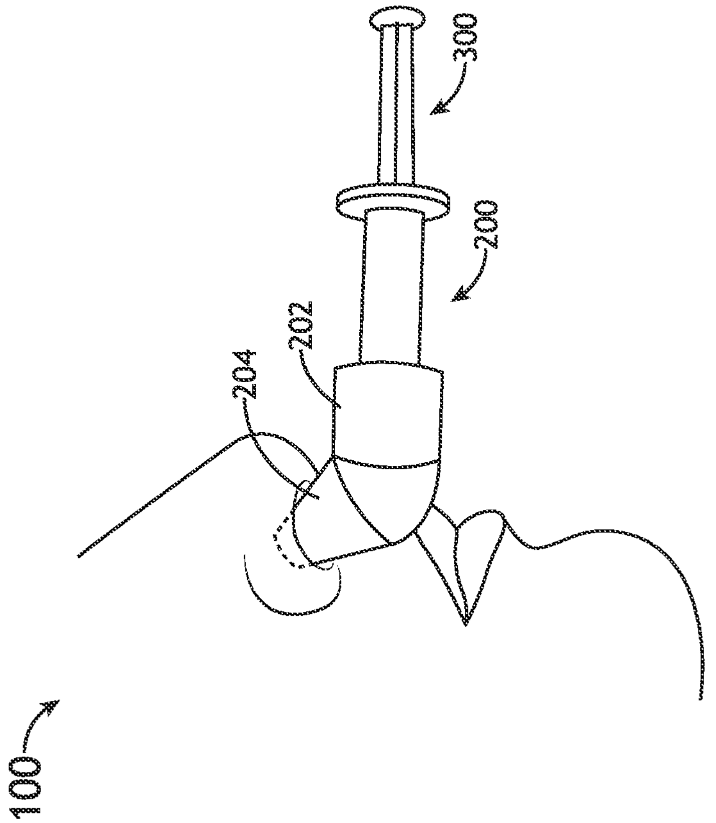
FIG. 11 is a schematic illustration of the NSC system, in accordance with one or more alternative embodiments of this disclosure.

FIG. 11 illustrates an alternative embodiment of the NSC system 100/NSC apparatus 200 where the nozzle 204 is angled to provide better ergonomics for the irrigation procedure. Instead of having to consider the proper angling of the NSC apparatus 200 to achieve nasopharyngeal cavity irrigation, the user simply has to hold the NSC apparatus 200 parallel to the ground. In some embodiments, the NSC apparatus 200 may further include a leveling mechanism to provide visual feedback of proper angle.

Figure 12:
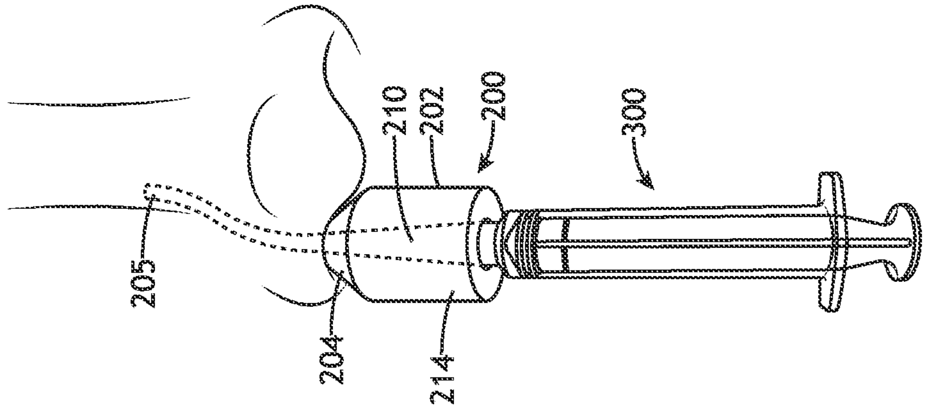
FIG. 12 is a schematic illustration of the NSC system, in accordance with one or more alternative embodiments of this disclosure.

FIG. 12 illustrates an alternative embodiment of the NSC system 100/NSC apparatus 200 where the nozzle 204 includes an extended opening 205 for the irrigation path 208 accomplished by a soft catheter that is inserted into the nose to facilitate direct irrigation of the target site. For example, the catheter may be coupled to the irrigation chamber 210. The drainage mechanism may remain the same as in other embodiments (e.g., same collection path 212 and associated structures as the embodiments illustrated in FIGS. 1A and 1B).

In some embodiments, the nozzle 204 may include a foam seal tip that is used to seal the nozzle 204 against the nasal orifice. For example, the tip of the nozzle 204 may have a similar structure to the compressible bladder described above, but instead, a pliable foam can be used to seal the nozzle 204 against the nasal orifice to prevent any fluid from leaking at the interface between the NSC apparatus 200 and the nasal cavity.

Figure 13:
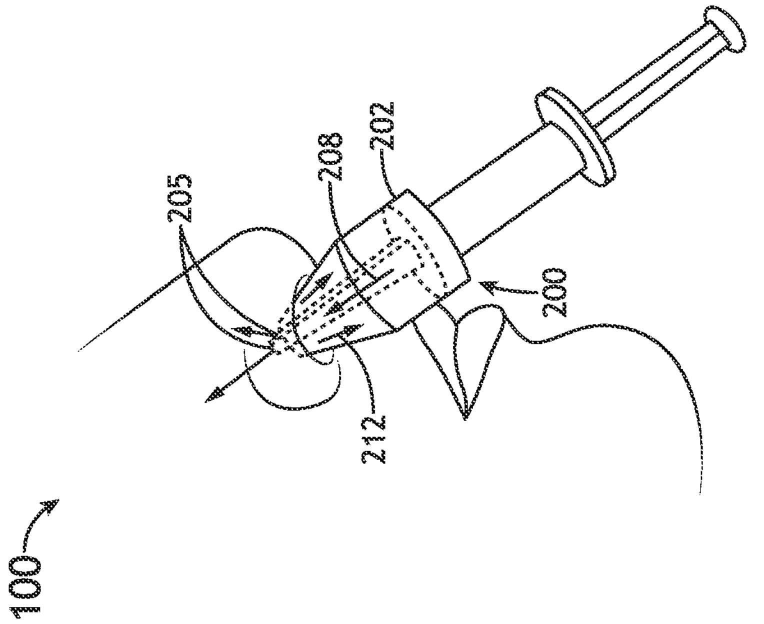
FIG. 13 is a schematic illustration of the NSC system, in accordance with one or more alternative embodiments of this disclosure.

FIG. 13 illustrates an alternative embodiment of the NSC system 100/NSC apparatus 200 where the nozzle 204 includes two or more openings 205 for the irrigation path 208. For example, in FIG. 13, the nozzle 204 includes a second irrigation outlet to compliment the main outlet port. The main outlet port will still irrigation the nasopharyngeal cavity while the second outlet is designed to irrigation the anterior nose chamber. This allows for dual site sample collection which may provide for improved sample quality/quantity.

Figure 14:
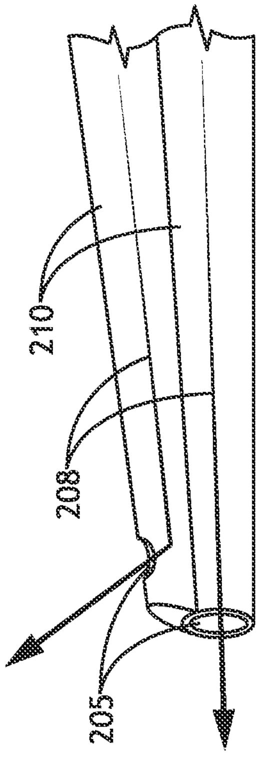
FIG. 14 is a schematic illustration of a portion of the nozzle of the NSC system, in accordance with one or more alternative embodiments of this disclosure.

FIG. 14 illustrates an alternative embodiment of the NSC apparatus 200 where the nozzle 204 includes two or more irrigation path openings 205 and also includes two irrigation paths 208 defined by parallel irrigation lumens/chambers 210. The dual chamber design can prevent pressure degradation that may be experienced when adding a second (or more) outlet ports.

Figure 15:
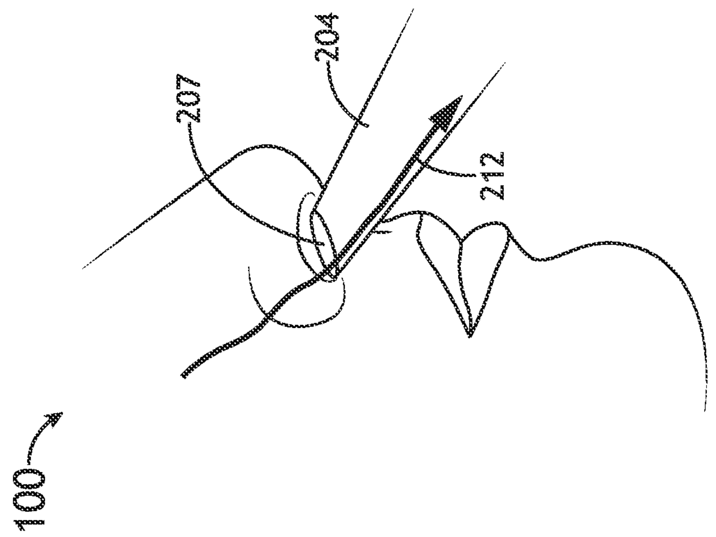
FIG. 15 is a schematic illustration of a portion of the nozzle of the NSC system, in accordance with one or more alternative embodiments of this disclosure.

FIG. 15 illustrates an alternative embodiment of the NSC apparatus 200 where the nozzle 204 has a tapered tip design to facilitate improved drainage. The tapered tip is designed to rest the tip of the nozzle 204 on the nasal floor facilitating drainage without the need for a seal against the nasal rim.

Figure 16B:
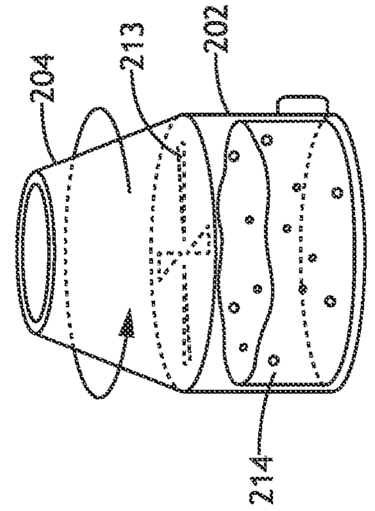
FIG. 16B is a schematic illustration of the NSC apparatus, in accordance with one or more alternative embodiments of this disclosure.
Figure 16A:
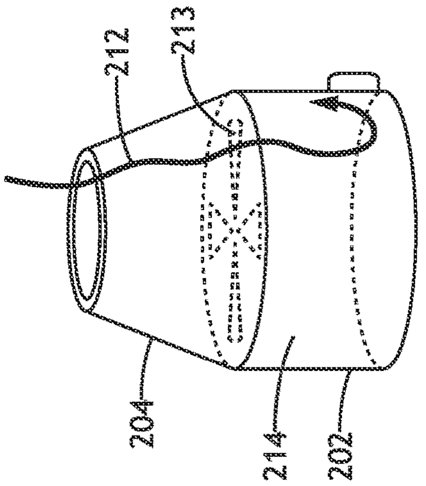
FIG. 16A is a schematic illustration of the NSC apparatus, in accordance with one or more alternative embodiments of this disclosure.

FIGS. 16A and 16B illustrate an alternative embodiment of the NSC apparatus 200 where the collection chamber 214 is configured to be sealed by a twist cap style barrier 213 that encloses the collection chamber 214 when a top portion (e.g., nozzle 204) of the NSC apparatus 200 is twisted relative to a bottom portion (e.g., device body 202) of the NSC apparatus 200. Once the irrigation fluid is recollected into the collection chamber 214 with a sample, the top portion of the NSC apparatus 200 is twisted clockwise or counterclockwise to close drainage channels at the twist cap style barrier 213 inside the NSC apparatus 200, sealing the sample inside for transport. This configuration allows the sample to be sealed within the NSC apparatus 200 without any need for a cap/stopper.

Figure 17:
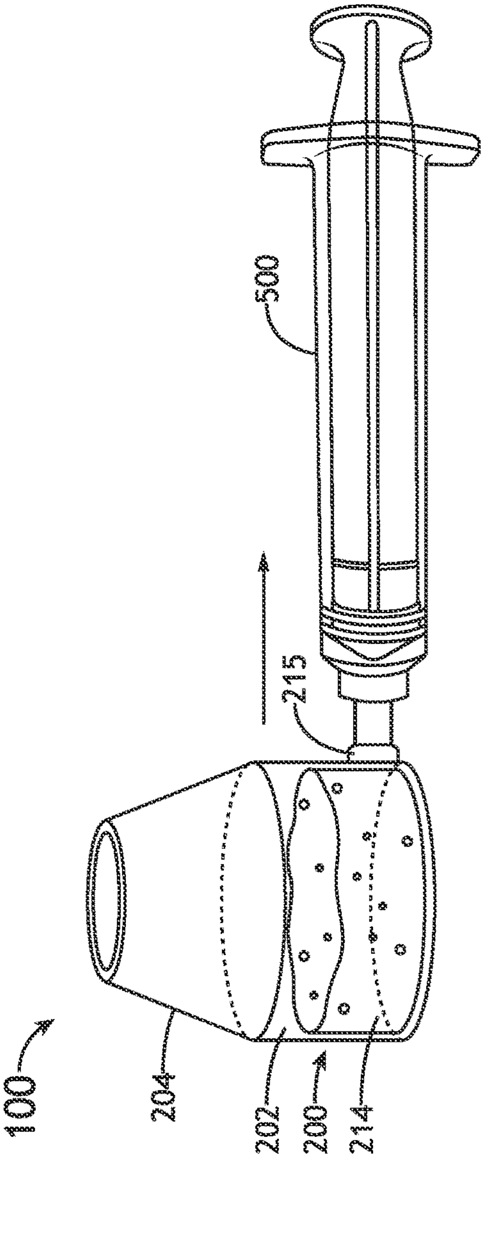
FIG. 17 is a schematic illustration of the NSC apparatus, in accordance with one or more alternative embodiments of this disclosure.

FIG. 17 illustrates an alternative embodiment of the NSC apparatus 200 where the collection chamber 214 includes a specimen collection port 215 formed through an outer surface of the device body 202. For example, the specimen collection port 215 may be located on an outer sidewall of the device body 202. After collecting a sample within the collection chamber 214, the sample can be removed from the NSC apparatus 200 through the specimen collection port 215. For example, a syringe 500 can be used to withdraw the sample from the collection chamber 214 via the specimen collection port 215.

Although the technology has been described with reference to the embodiments illustrated in the attached drawing figures, equivalents may be employed, and substitutions may be made herein without departing from the scope of the technology as recited in the claims. Components illustrated and described herein are examples of devices and components that may be used to implement the embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. An apparatus for collecting a nasal specimen, comprising:
 a device body;
 a connector at a proximal end of the device body, the connector configured to couple a port at the proximal end of the device body to a syringe containing a fluid;
 a nozzle at a distal end of the device body, the nozzle configured to interface with a nasal cavity;
 an irrigation path and an irrigation chamber centrally disposed within the device body, wherein the irrigation chamber is configured to receive the fluid from the syringe via the port at the proximal end of the device body, and wherein the irrigation path extends to a circular opening of the nozzle and is configured to direct the fluid from the irrigation chamber into the nasal cavity in order to dislodge a sample from the nasal cavity; and
 a collection path and a collection chamber surrounding the irrigation path and the irrigation chamber within the device body, wherein the collection path extends from an annular opening of the nozzle and is configured to passively direct at least a portion of the fluid and the sample dislodged from the nasal cavity into the collection chamber, wherein the collection chamber has an open end at least partially defined by the collection path and a closed end opposite the open end, wherein the collection chamber has a fixed volume, wherein the collection path is separate from the irrigation path, and wherein the collection path and the irrigation path are coaxial within the device body.

2. The apparatus of claim 1, wherein the fluid comprises a saline solution.

3. The apparatus of claim 1, wherein the collection chamber contains at least one of a specimen preservation agent or a testing agent.

4. The apparatus of claim 1, further comprising:
 a cap configured to enclose the collection chamber when the cap is coupled to the nozzle.

5. The apparatus of claim 1, wherein to dislodge the sample from the nasal cavity, the nozzle is configured to direct the fluid into the nasal cavity at an irrigation pressure in a range of 5 to 20 pounds per square inch (PSI).

6. A system for collecting a nasal specimen, comprising:
 a syringe containing a fluid; and
 an apparatus configured to be removably coupled to the syringe, the apparatus comprising:
 a device body;
 a connector at a proximal end of the device body, the connector configured to couple a port at the proximal end of the device body to the syringe;
 a nozzle at a distal end of the device body, the nozzle configured to interface with a nasal cavity;
 an irrigation path and an irrigation chamber centrally disposed within the device body, wherein the irrigation chamber is configured to receive the fluid from the syringe via the port at the proximal end of the device body, and wherein the irrigation path extends to a circular opening of the nozzle and is configured to direct the fluid from the irrigation chamber into the nasal cavity in order to dislodge a sample from the nasal cavity; and
 a collection path and a collection chamber surrounding the irrigation path and the irrigation chamber within the device body, wherein the collection path extends from an annular opening of the nozzle and is configured to passively direct at least a portion of the fluid and the sample dislodged from the nasal cavity into the collection chamber, wherein the collection chamber has an open end at least partially defined by the collection path and a closed end opposite the open end, wherein the collection chamber has a fixed volume, wherein the collection path is separate from the irrigation path, and wherein the collection path and the irrigation path are coaxial within the device body.

7. The system of claim 6, wherein the fluid comprises a saline solution.

8. The system of claim 6, wherein the collection chamber contains at least one of a specimen preservation agent or a testing agent.

9. The system of claim 6, further comprising:
 a cap configured to enclose the collection chamber when the cap is coupled to the nozzle.

10. The system of claim 9, further comprising:
 a portable enclosure with distinct cutouts configured to hold the apparatus, the syringe, and the cap.

11. The system of claim 10, wherein the portable enclosure includes a lid with instructions for using the system printed or adhered to an inner surface of the lid.

12. The system of claim 6, wherein to dislodge the sample from the nasal cavity, the nozzle is configured to direct the fluid into the nasal cavity at an irrigation pressure in a range of 5 to 20 pounds per square inch (PSI).

13. A method of collecting a nasal specimen, comprising:
 interfacing a nozzle at a distal end of a device body with a nasal cavity, the device body including:
 a connector at a proximal end of the device body, the connector configured to couple a port at the proximal end of the device body to a syringe containing a fluid;
 an irrigation path and an irrigation chamber centrally disposed within the device body, wherein the irrigation chamber is configured to receive the fluid from the syringe via the port at the proximal end of the device body, and wherein the irrigation path extends from the irrigation chamber to a circular opening of the nozzle; and
 a collection path and a collection chamber surrounding the irrigation path and the irrigation chamber within the device body, wherein the collection path extends from an annular opening of the nozzle to the collection chamber, wherein the collection chamber has an open end at least partially defined by the collection path and a closed end opposite the open end, wherein the collection chamber has a fixed volume, wherein the collection path is separate from the irrigation path, and wherein the collection path and the irrigation path are coaxial within the device body;
 actuating fluid from the syringe through the irrigation path into the nasal cavity in order to dislodge a sample from the nasal cavity; and collecting, in the collection chamber via the collection path, at least a portion of the fluid and the sample dislodged from the nasal cavity.

* * * * *